(12) United States Patent
Remirez Miguel et al.

(10) Patent No.: US 12,251,482 B2
(45) Date of Patent: Mar. 18, 2025

(54) DISINFECTION SYSTEM FOR WOOD BARRELS

(71) Applicant: CLEANWOOD TECHNOLOGY S.L., Alava (ES)

(72) Inventors: Eduardo José Remirez Miguel, Logroño (ES); Jorge Remirez Miguel, Logroño (ES)

(73) Assignee: CLEANWOOD TECHNOLOGY S.L., Lanciego (ES)

( * ) Notice: Subject to any disclaimer, the term of this patent is extended or adjusted under 35 U.S.C. 154(b) by 990 days.

(21) Appl. No.: 17/052,120

(22) PCT Filed: May 7, 2019

(86) PCT No.: PCT/EP2019/061676
§ 371 (c)(1),
(2) Date: Oct. 30, 2020

(87) PCT Pub. No.: WO2019/215146
PCT Pub. Date: Nov. 14, 2019

(65) Prior Publication Data
US 2021/0121589 A1    Apr. 29, 2021

(30) Foreign Application Priority Data

May 8, 2018 (EP) .................................... 18382315

(51) Int. Cl.
| | |
|---|---|
| *A61L 2/12* | (2006.01) |
| *A61L 2/24* | (2006.01) |
| *B27K 5/00* | (2006.01) |
| *H05B 6/64* | (2006.01) |
| *H05B 6/68* | (2006.01) |
| *H05B 6/72* | (2006.01) |
| *H05B 6/78* | (2006.01) |
| *H05B 6/80* | (2006.01) |
| *H05B 6/66* | (2006.01) |
| *H05B 6/70* | (2006.01) |

(Continued)

(52) U.S. Cl.
CPC .................... *A61L 2/12* (2013.01); *A61L 2/24* (2013.01); *B27K 5/0055* (2013.01);
(Continued)

(58) Field of Classification Search
CPC .......... A61L 2/10; A61L 2/24; A61L 2202/11; A61L 2202/122; A61L 2202/23;
(Continued)

(56) References Cited

U.S. PATENT DOCUMENTS 5,302,343 A * 4/1994 Jacob ........................ A61L 2/12
422/23
2003/0049162 A1* 3/2003 Blondeau .................. A61L 2/12
422/21

(Continued)

FOREIGN PATENT DOCUMENTS

WO    WO-9808359 A1    2/1998

OTHER PUBLICATIONS

International Search Report in PCT/EP2019/061676, mailed Sep. 2, 2019, 4 pages.

(Continued)

*Primary Examiner* — Sean E Conley
*Assistant Examiner* — Brendan A Hensel
(74) *Attorney, Agent, or Firm* — Weaver Austin Villeneuve & Sampson LLP (57) ABSTRACT

Different aspects of the invention refer to a disinfection apparatus, and corresponding method, for wood barrel disinfection using microwave shock pulse, MwSP, technology for the complete elimination of microbial populations. This is accomplished by a system which ensures deep and complete disinfection, however such that the temperature is maintained below material degradation level. Complete disinfection is achieved due to effectiveness up to the deepest layers. The wooden barrel material is however preserved, due to the non-harmful nature of the dosage regime programmed into the radio frequency emission.

8 Claims, 13 Drawing Sheets

(52) U.S. Cl.
CPC ......... *H05B 6/6402* (2013.01); *H05B 6/6447* (2013.01); *H05B 6/68* (2013.01); *H05B 6/72* (2013.01); *H05B 6/78* (2013.01); *H05B 6/80* (2013.01); *A61L 2202/11* (2013.01); *A61L 2202/121* (2013.01); *A61L 2202/122* (2013.01); *A61L 2202/14* (2013.01); *A61L 2202/23* (2013.01); *H05B 6/645* (2013.01); *H05B 6/666* (2013.01); *H05B 6/707* (2013.01); *H05B 2206/045* (2013.01)

(58) Field of Classification Search
CPC .. A61L 2/12; A61L 2202/121; A61L 2202/14; B27K 5/0055; H05B 6/6402; H05B 6/6447
See application file for complete search history.

(56) References Cited

U.S. PATENT DOCUMENTS

| | | | | |
|---|---|---|---|---|
| 2011/0014331 | A1* | 1/2011 | Stull, Jr. | H01J 23/38 426/241 |
| 2012/0164022 | A1* | 6/2012 | Muginstein | H05B 6/72 405/128.7 |
| 2016/0249416 | A1 | 8/2016 | Elboim et al. | |
| 2019/0328912 | A1* | 10/2019 | Staid | A61L 2/24 |

OTHER PUBLICATIONS

Electrolux: Frigidaire Professional 30" Built-In Convection Microwave Oven with Drop-Down Door (FPMO3077T) Manual, Specification Sheet, 2017, 3 pages, original URL: http://manuals.frigidaire.com/prodinfo_pdf/Specsheets/FPMO3077T_1017_EN.pdf [retrieved on Nov. 7, 2018—no longer available]. Current copy obtained from URL: https://s1.img-b.com/compactappliance.com/mediabase/specifications/frigidaire/1543706/frigidaire-fpmo3077t-specification-sheet.pdf [retrieved on Mar. 5, 2024].
EP Extended European Search Report dated Apr. 1, 2019 in EP Application No. 18382315.2.
EP Office Action dated May 23, 2022 in EP Application No. 18382315.2.
EP Partial European Search Report dated Nov. 16, 2018 in EP Application No. 18382315.2.
International Preliminary Report on Patentability and Written Opinion dated Nov. 19, 2020 in PCT Application No. PCT/EP2019/061676.

* cited by examiner

DISINFECTION SYSTEM FOR WOOD BARRELS

CROSS-REFERENCE TO RELATED APPLICATIONS

This application is a U.S. national stage entry under 35 U.S.C. § 371 of International Application No. PCT/EP2019/061676, filed May 7, 2019, entitled "DISINFECTION SYSTEM FOR WOOD BARRELS," which claims priority to and the benefit of EP patent application Ser. No. 18/382,315.2, filed May 8, 2018, entitled "DISINFECTION SYSTEM FOR WOOD BARRELS," the disclosures of which are incorporated herein by reference in their entireties.

FIELD OF THE INVENTION

This invention relates to the field of disinfection of wooden barrels via the application of microwave radiation.

BACKGROUND

Barrels used for maturing and storing wine are typically made from wood due to its inherent properties. However, wooden barrels are not cheap, and they cannot simply be discarded after a single use, due to lack of general availability of wood. Some valuable wood, such as oak, is depleting at an increasing rate.

Due to the porous nature of wood, conditions exist which are ripe for bacterial multiplication. The wooden barrels have to be disinfected periodically as microbial populations grow and nest within them. Such populations can be found not only on the inner surface of the barrel which is normally in contact with the wine, but typically they also nest deep within the wood itself as well as over its external surface. Whereas bacterial populations form part of the wine maturing process and also of the global taste of the wine, they negatively affect the properties of the next wine to be matured in the same barrel.

Several wood disinfection schemes exist which when applied to wooden barrels aim at reducing microbial populations whilst re-utilizing the barrel for the next batch. Such conventional schemes suffer from a number of drawbacks. One problem is that of superficial disinfection, as they are not able to target deep into the wood, such as the inner layers of the wood, where the bacteria nest, thereby not completely eliminating the infection. Another severe problem is that of material destruction, as the most effective treatments in terms of microbe elimination are also highly corrosive, actually destroying the material being treated. In relation to wood, they render the wine barrels not useable only after very few treatments, resulting in a non-recyclable or non-sustainable treatment. Most chemical treatments, as well as thermal treatment by high temperatures exceeding 65° C.-70° C., produce this undesirable effect. Some schemes are actually dangerous, since they require diverse toxic procedures which are dangerous for manipulation by humans, and also leave traces which eventually might appear in the food products being carried, such as the wine in the barrels. Another drawback of conventional systems is their transport carbon footprint and exposure; due to the complex nature of conventional disinfection procedures, especially those using corrosive chemicals, the barrels must be transported to the disinfection site. Apart from increasing the carbon footprint of such treatments, a considerable drawback is that of further contamination of the barrels as they leave their stable and controlled eco-system. Due to the delicate nature of the wine maturing process, the change in temperature and airborne organisms can detrimentally affect the quality of the final product. These systems also consume large amounts of water and electricity.

Therefore a need exists to effectively solve the above-mentioned problems.

SUMMARY

It is therefore an object of the present invention to provide solutions to the above mentioned problems. In particular, it is an object of the invention to provide a novel disinfection apparatus, and corresponding method, for wood barrel disinfection using microwave shock pulse, MwSP, technology for the complete elimination of microbial populations. The technology operates by causing molecular vibrations in the fabric of the wood and the internal generation of ozone, which in combination, cause a hostile environment for the reproduction or growth of microbes. The inventors have proven how the application of microwave pulses is extremely effective for the complete disinfection of the wood being treated. More importantly, since the temperature of the wood is actively monitored, and not allowed beyond its destructive threshold temperature, the organoleptic properties of the wood are maintained, thereby optimising the disinfection process for wood which will be used with food products. In particular, the disinfected barrels do not negatively affect the taste or bouquet of the wine being matured therein.

This is accomplished by a system which ensures deep and complete disinfection, however such that the temperature is maintained below material degradation level. Complete disinfection is achieved due to effectiveness up to the deepest layers. The wooden barrel material is however preserved, due to the non-harmful nature of the dosage regime programmed into the radio frequency emission. It is also a safe procedure, due to the inexistence of contact with operators, as well as inexistence of traces in the food products being carried. Due to its simplicity, on-site treatment is enabled, as the technology permits implementing an easily transportable system for speedy treatment, which is installed on-site at the user's premises, minimising carbon footprint as well as external contamination. This is turn leads to a sustainable system, due to the reduction in resource consumption.

Therefore, it is one object of the present invention to provide a disinfection apparatus, and a corresponding method of disinfection, as defined by the accompanying claims. Preferred embodiments are defined by the dependent claims.

The invention provides methods and devices that implement various aspects, embodiments, and features of the invention, and are implemented by various means.

The various means may comprise, for example, hardware, software, firmware, or a combination thereof, and these techniques may be implemented in any single one, or combination of, the various means. The various means disclosed may be implemented as software modules within a computer program.

BRIEF DESCRIPTION OF THE DRAWING(S)

The features and advantages of the present invention will become more apparent from the detailed description set forth below when taken in conjunction with the drawings in which like reference characters identify corresponding elements in the different drawings. Corresponding elements may also be referenced using different characters.

DETAILED DESCRIPTION OF THE INVENTION

Figure 1:
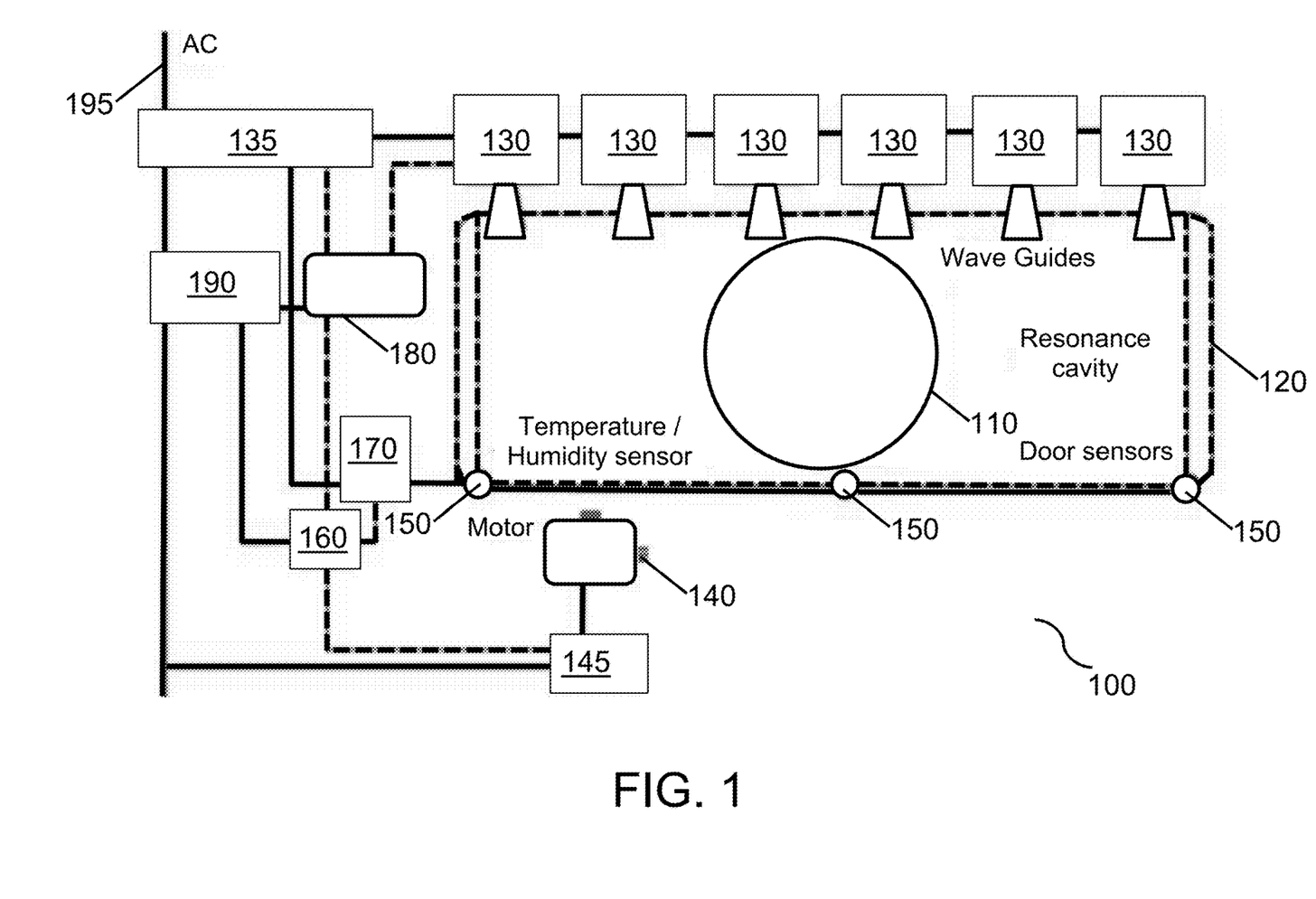
FIG. 1 depicts a lateral view of the disinfection apparatus according to one aspect.
Figure 2:
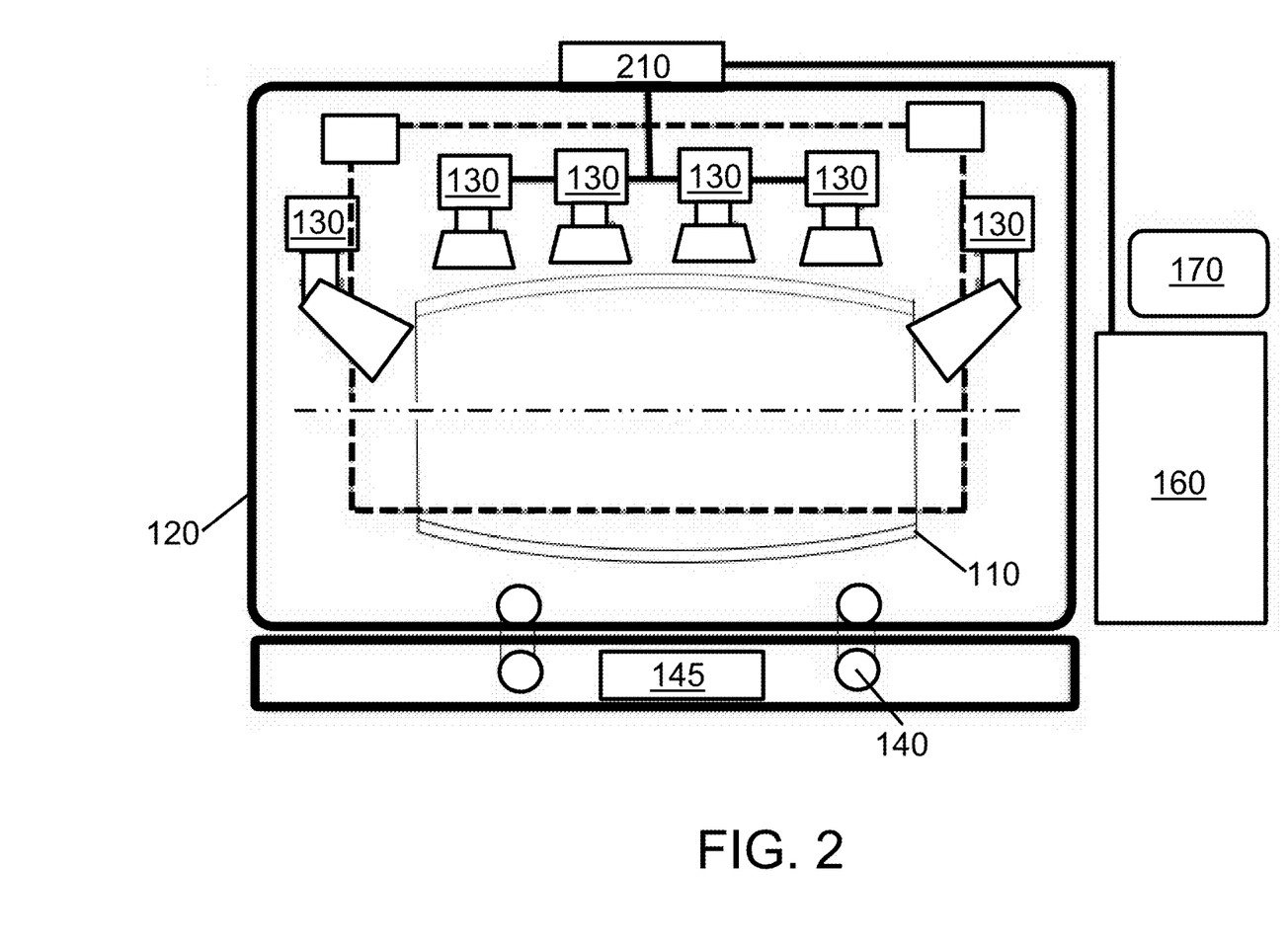
FIG. 2 depicts a longitudinal view of the disinfection apparatus according to one aspect.

FIG. 1 depicts a lateral view of the disinfection apparatus 100 whereas FIG. 2 depicts a longitudinal view of the disinfection apparatus. In FIG. 1, the barrel 110 is seen from one of its ends, whereas in FIG. 2 it is depicted sideways. The barrels are placed such that they can be rolled. In this aspect they can be rolled in and out of either ends of the apparatus (left side of FIG. 3), or placed so that the apparatus can house the barrel to be treated by elevating an descending (right side of FIG. 3). The disinfection is to be applied preferably to micro-organisms known as Brettanomyces in oak wine barrels, although it can be applied also to other microbes existent in other materials as well.

The disinfection apparatus 100 comprises a chamber 120, or resonance cavity, for hosting the barrel. The cavity may have in its simplest form a rectangular configuration, however a polyhedric configuration maximises uniform radiation within the chamber. The junctions between the chamber opening and the hatchets or doors are lined with metal-covered rubber-strips for ensuring maximum electromagnetic sealing.

Figure 3:
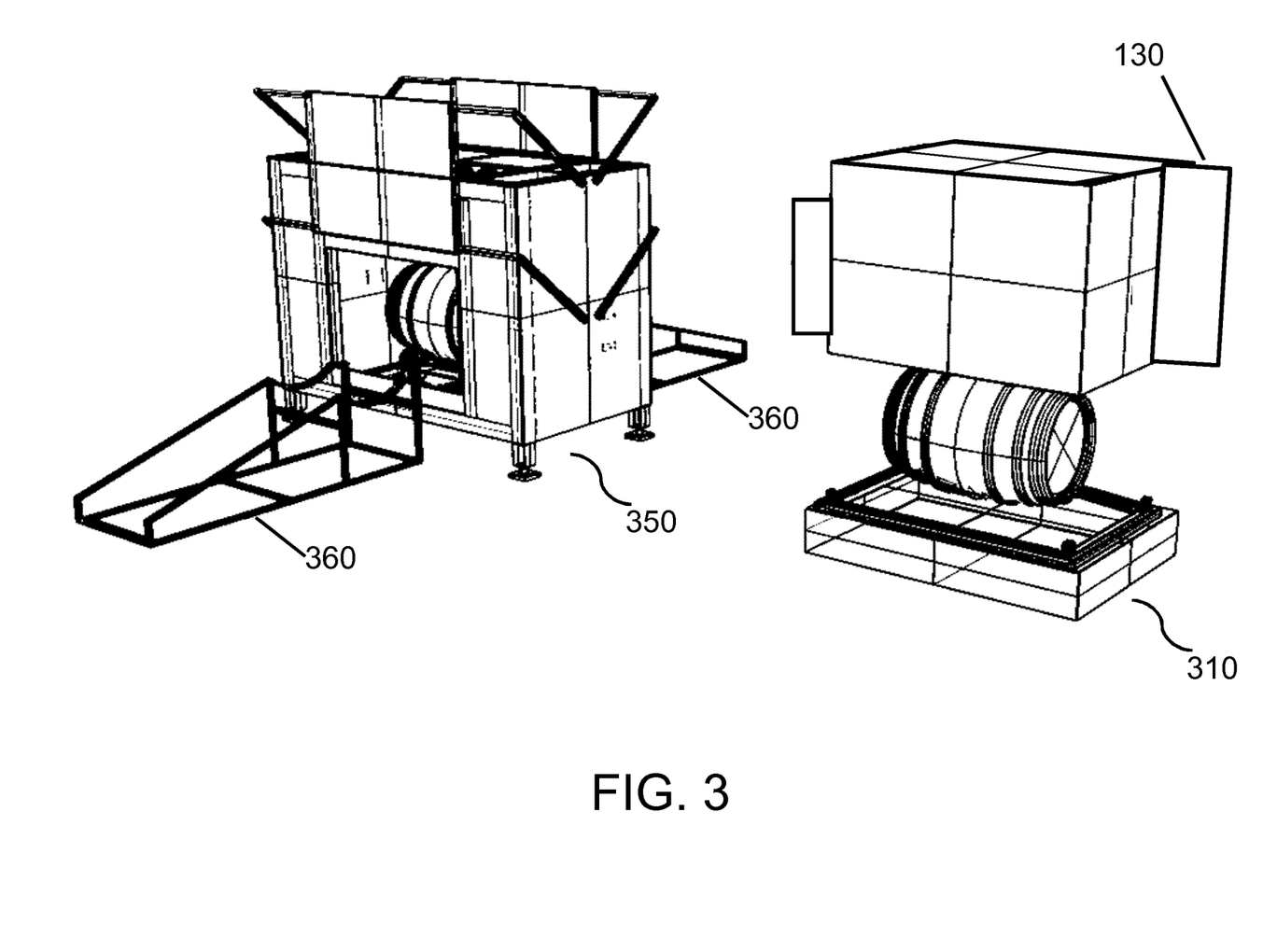
FIG. 3 depicts an example disinfection apparatus wherein the barrels are loaded into, and unloaded out of, the chamber laterally, and an example static disinfection apparatus.

In one configuration 310, such as depicted on the right side in FIG. 3, the disinfecting apparatus is configured to rise and lower and to receive a barrel through an opening. In this configuration the disinfection is performed statically, that is, without the barrel moving. Instead of elevating or descending the mobile chamber, a hatchet may be used instead. Although the construction is simpler, it is less comfortable for the user to load and unload the barrels, and also takes more time.

In another aspect, the disinfection apparatus comprises a running belt. Together with the aid of stops, or rollers, this movement causes the barrel to rotate on its axis, thereby ensuring uniform application of radiation throughout its whole volume uniformly. In another aspect 350, shown on the left side of FIG. 3, the running belt serves to allow dynamic disinfection, as it is configured with loading and unloading units 360 to roll-in and roll-out barrels continuously. This configuration is best suited for integrating the disinfecting apparatus into an existing production line, such as existing in barrel production or refurbishing facility. The motor 140 for operating the running belt is controlled by a speed controller 145.

Figure 7:
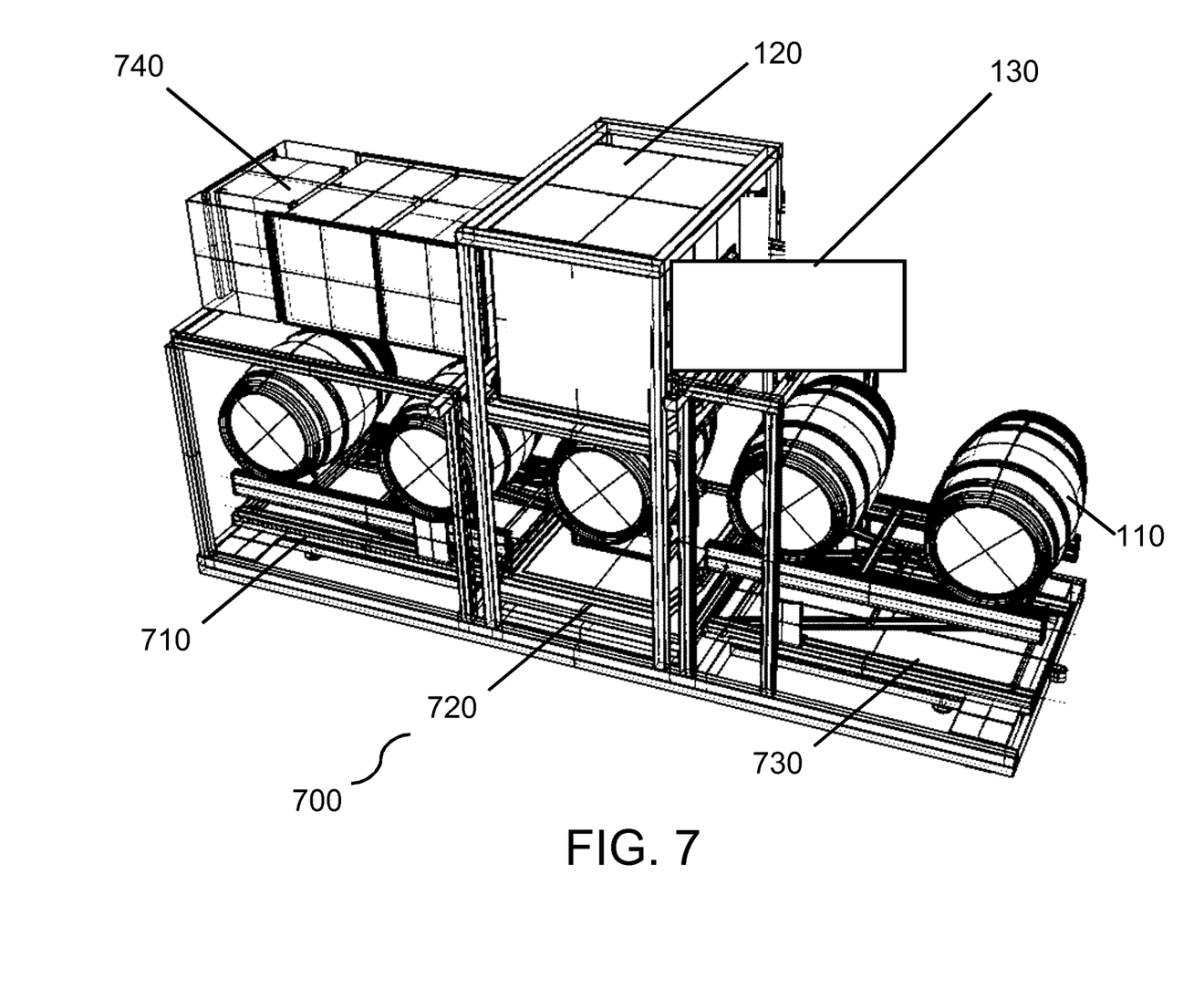
FIGS. 7 and 8 depict an example disinfection apparatus according to another aspect wherein the barrels are elevated into, and descended out of, the chamber through a bottom opening.
Figure 8:
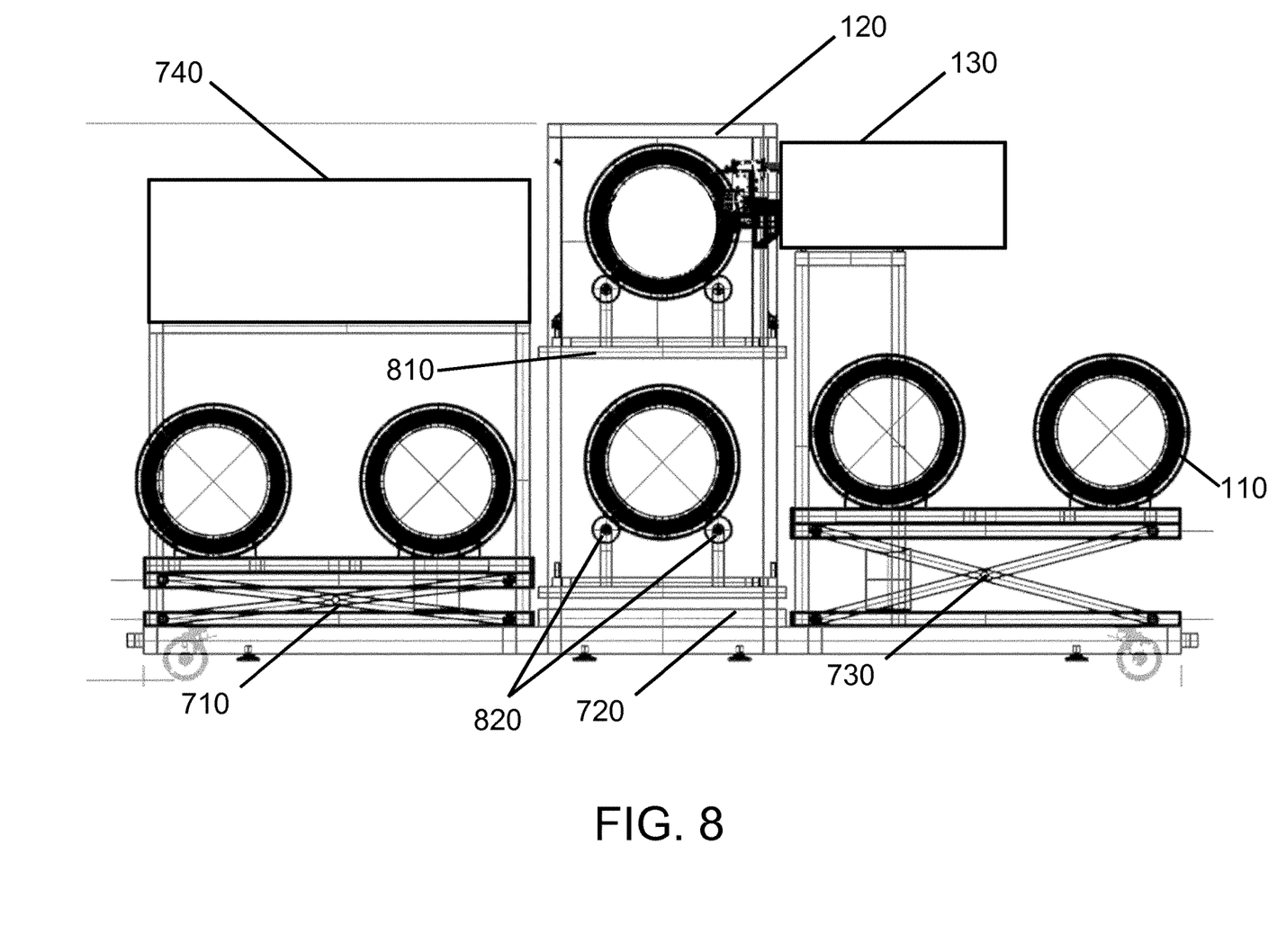

In yet another aspect, shown in FIGS. 7 and 8, the disinfection is dynamic, allowing the constant loading and unloading of barrels. In one aspect the barrels are elevated into, and descended out of, the chamber through a bottom opening, whereas in another aspect it is the cavity which descends and ascends.

Returning to FIG. 1 or FIG. 2, at least one microwave radiating means 130, comprising each a source of microwave radiation and a waveguide, is arranged above the barrel within the chamber. The source of microwave radiation is configurable to emit radiation in pulses of variable frequency, intensity and pulse duration. In one aspect, a plurality of radiating means are provided preferably arranged longitudinally along the chamber in order to uniformly radiate the barrel along the full length of the chamber. In another aspect, better seen in FIG. 2, a plurality of radiating means are provided transversally spread in order to uniformly radiate the full length of the barrel. In this aspect, it is advantageous to configure the most lateral radiating means partially along the sides of the chamber, lower in height, in order to radiate the barrel laterally, or slightly diagonally, through its openings on either end. This different radiation angle increases the efficacy of the disinfection within the barrel, as well as maximises uniform radiation to all corners of the barrel. The radiating means are powered by a radio frequency power supply 135.

Figure 9:
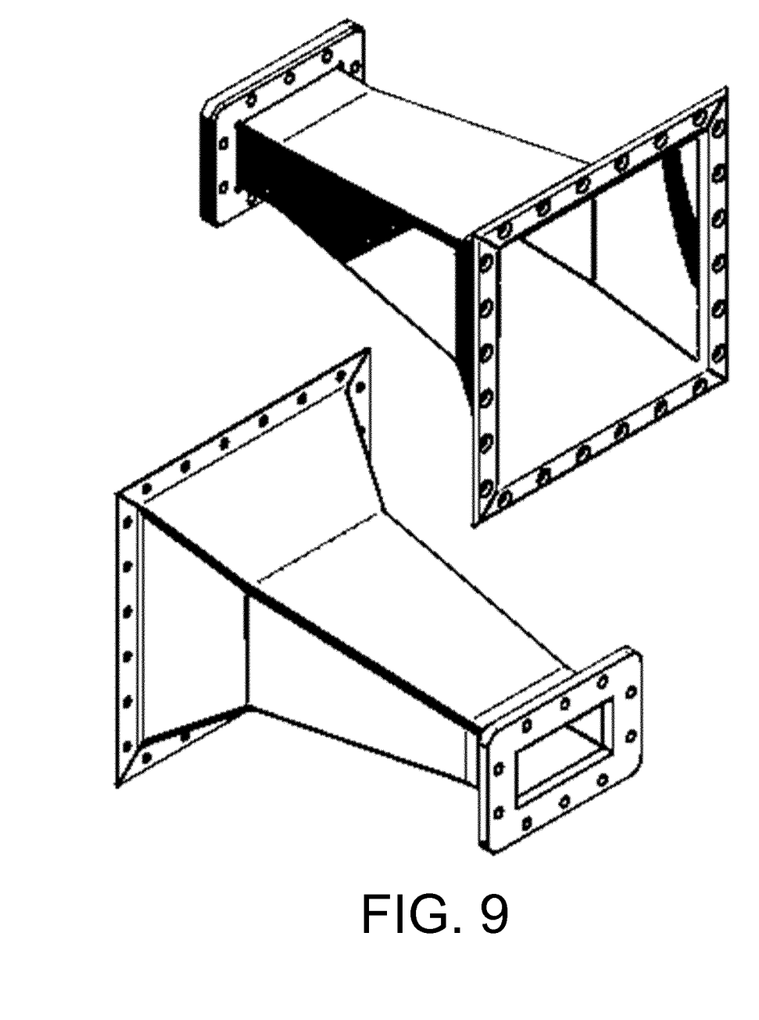
FIGS. 9 and 10 depict the configuration of the microwave antenna.
Figure 10:
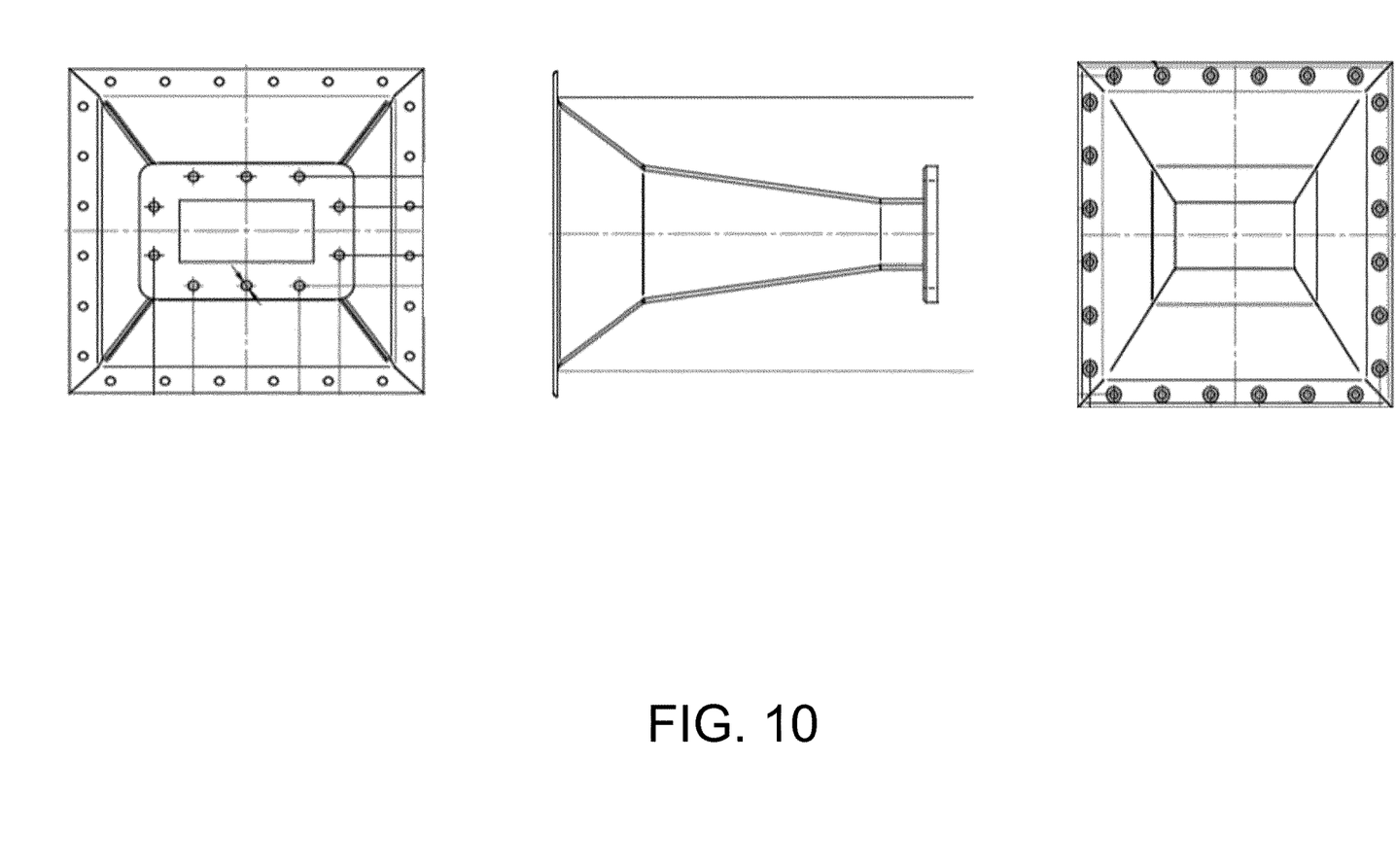

FIGS. 9 and 10 depict the configuration of the wave guide, or microwave antenna. The antenna has been configured in order to ensure uniform and constant radiation to the required depth within the chamber. Together with the rotating means, this causes the complete disinfection of the wooden barrels as they are rotated along their longitudinal axis.

The disinfecting apparatus also comprises at least one sensor 150 for providing live control of the treatment process. Radio frequency sensors determine the level of radiation within the chamber. Temperature sensors determine the internal temperature of the chamber. Door sensors determine when the doors are open or closed. A programmable logic controller, or processing means 160, continuously collects the data from the different sensors and uses them to modulate the disinfection process.

In one aspect, the disinfecting apparatus comprises safety means 170 which independently, by using the collected information, triggers an alarm system in case any of the readings are above a predetermined danger threshold. In this manner maximum safety is guaranteed autonomously.

In another aspect, the disinfecting apparatus comprises uniformity means 180 for detecting zones of non-uniform irradiation, and providing feedback for fine-tuning the emission parameters of the microwave pulses ensuring homogenized treatment. In one aspect a predetermined depth, called the point-of-interest POI, from the chamber ceiling is monitored in order to ascertain its radiation level, and vary the emission parameters to maintain a stable level. In another aspect, zones typically under any metallic element part of the wood barrels, such as the hoops and rivets necessary to hold the staves together, may be monitored to determined their level with respect to the POI, and vary the radiation parameters in order to ensure successful disinfection also in these problematic zones.

The whole apparatus is powered by powering means 190, which draws its electric power supply from alternating current power supply line 195. In another aspect, the disinfecting means comprises a refrigeration unit 210 for controlling and maintaining the temperature within a normal operating range.

Figure 13:
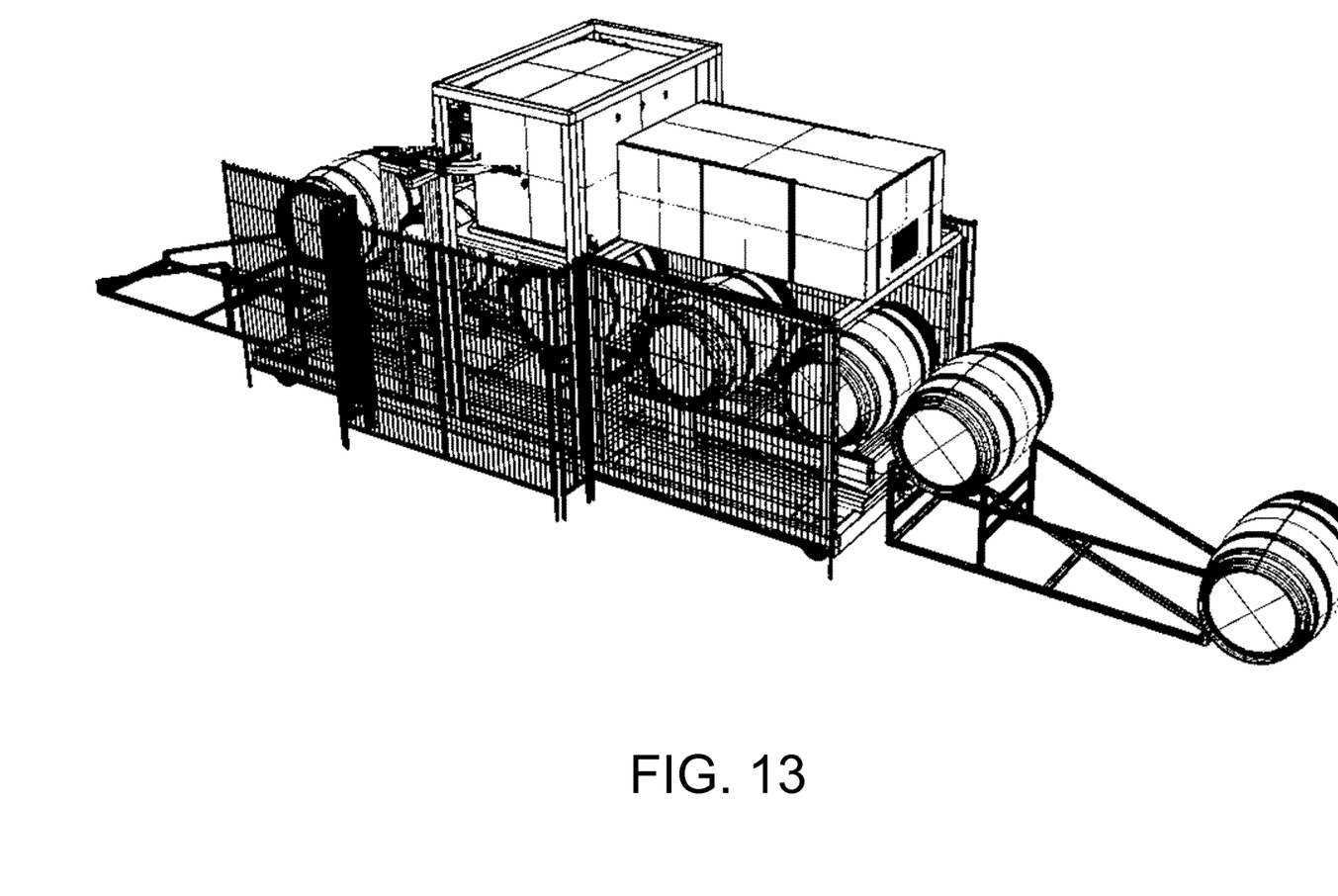
FIG. 13 depicts an example disinfection apparatus according to another aspect wherein the barrels are loaded and unloaded via ramps and the cavity is mobile as it is elevated and descended onto the barrels.

In one aspect the disinfection is dynamic allowing the constant loading and unloading of barrels. In the aspect of FIG. 13, as well as in the aspect of FIGS. 7 and 8, the barrels are elevated into, and descended out of, the chamber through a bottom opening. Whereas in FIG. 13 they are loaded and unloaded via a ramp, in FIGS. 7 and 8 this is achieved via the elevation means. This loading configuration in which the chamber is lowered onto the barrels, instead of the barrels being rolled into a fixed chamber has been so designed in order to minimise the detrimental effects to the different elements of the chamber 120 and within the chamber 120.

Figure 11:
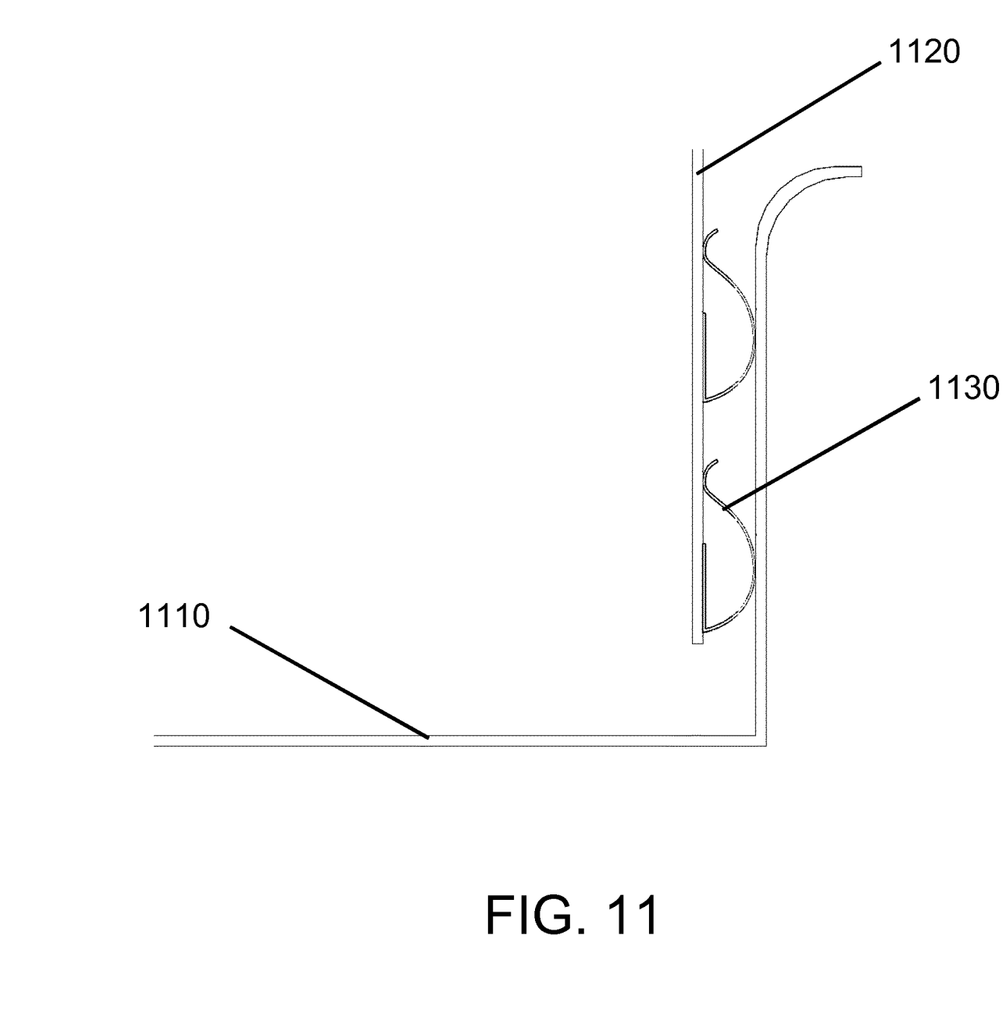
FIGS. 11 and 12 depict the configuration of the coupling elements.
Figure 12:
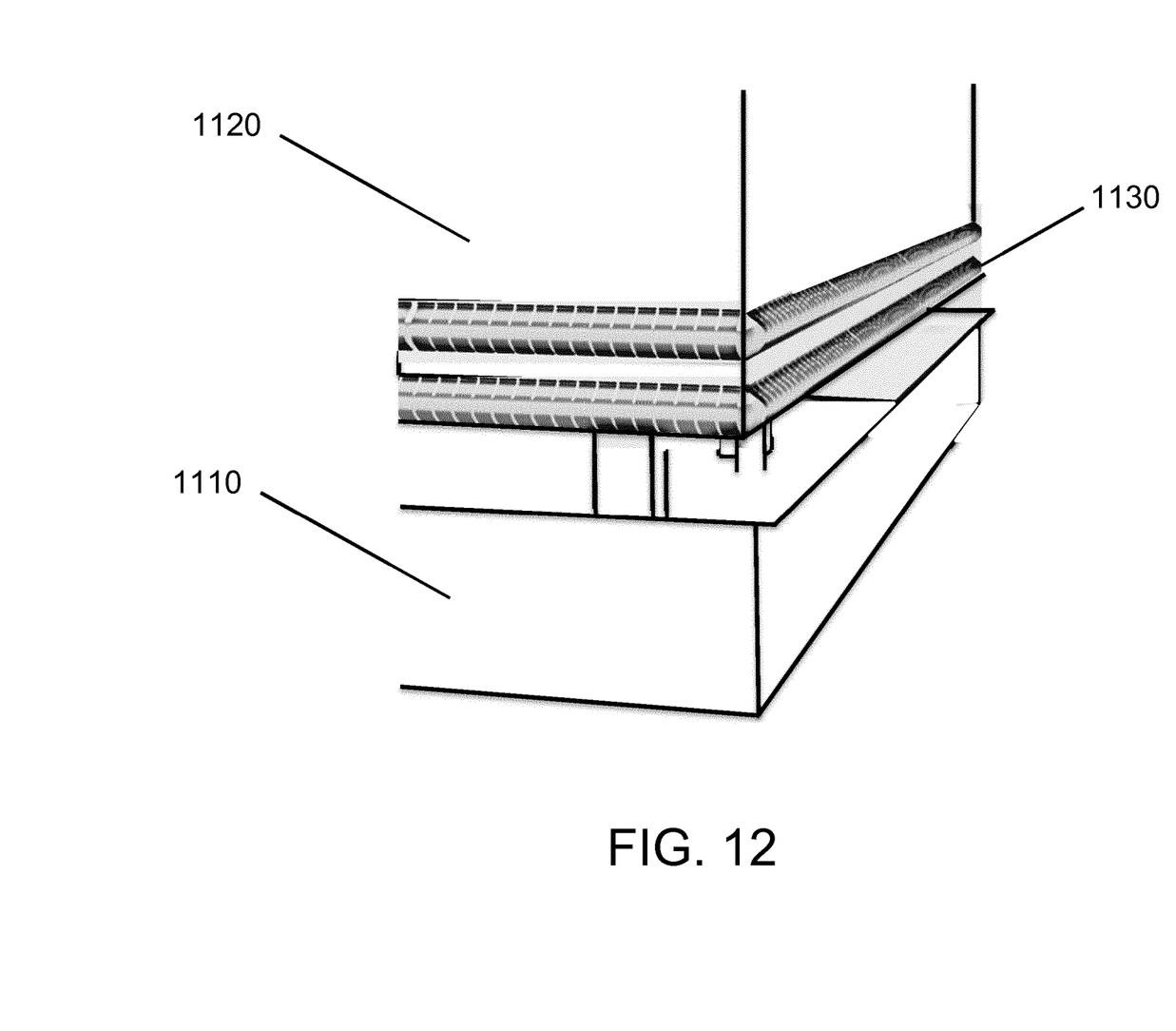

In both configurations, it was ascertained that the doors eventually cause radiation spillage. Hence, in the configuration of FIG. 8, only a single door 810 is provided, reducing any spillage or damage. Further, there is no impact to the wheels or rotating structure due to the entry or exit of the barrels. Minimum radiation spillage is guaranteed by a coupling mechanism which electromagnetically seals the cavity. FIG. 11 depicts a plurality of coupling elements 1130 arranged between the chamber housing 1120 and the floor 1110 on which the barrel is placed. Once closed, as can be seen in FIG. 12, the metallic floor 1110 and the metallic housing 1120 are electrically coupled via the coupling elements 1130. Each coupling element is metallic, and designed with as a flexible structure so that it can be compressed allowing a degree of tolerance as the chamber 1120 is lowered onto the floor 1110 in an automatized process. Its flexibility allows it always to be in contact with both chamber and floor. As can be seen the plurality of coupling elements are arranged along the sides of the chamber, at its lower end which will come into contact with the floor. At least one row of coupling elements is necessary, however two rows ensures maximum sealing.

Back to the aspect of FIG. 7, at the beginning of a new cycle, the barrel is rolled from loading means 710 onto the elevation means 720, which can be scissor-type elevators. The bottom opening of the chamber 120 is then shut by a door 810 and the disinfection process is activated. After the end of the disinfection, the door is opened and the scissor-type elevators 720 are descended, allowing the barrels to be rolled onto the unloading section 730. This configuration is less detrimental to the integrity of the disinfection apparatus, allowing extending its efficient life. FIG. 8 depicts the barrel 110 in both states on the elevation means 720, before elevation at the bottom, and after elevation at the top with the door 810 shut. Rotating means 820 are also depicted, which cause the rotation of the barrel around its longitudinal axis. Rotation means 820 comprises four rotatory wheels activated by motor 140 and controlled by controller 145. The remaining components of the disinfection apparatus, such as speed controller 145, processing means 160, safety means 170, uniformity means 180, or powering means 190, are stored within the storage module 740.

Figure 6:
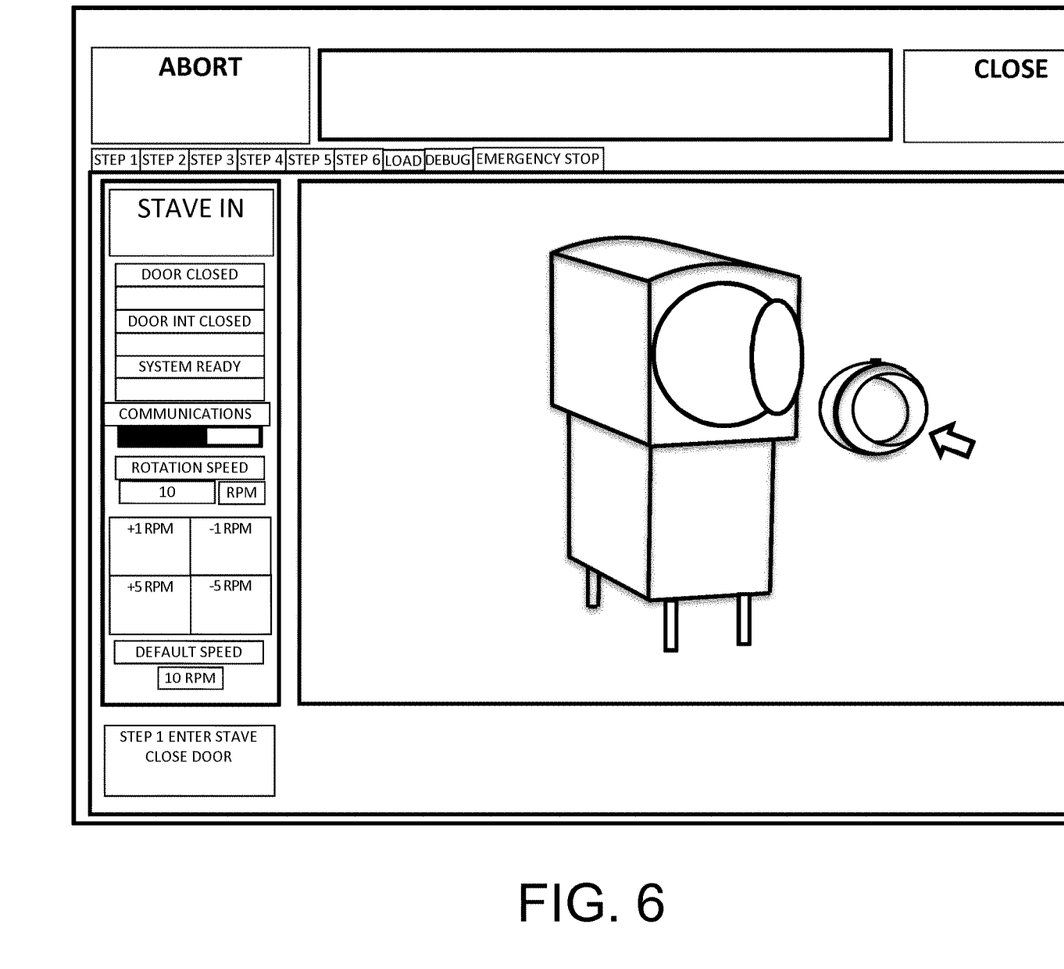
FIG. 6 depicts an example graphical user interface for controlling the disinfection.

FIG. 6 depicts the graphical user interface of the software, or computer program, which allows the operator to control the method of disinfection. In a first setup phase of operation, the barrel is loaded into the chamber. In the next step the disinfection process is started by activating the rotating means, which causes the barrel to rotate upon its longitudinal axis. In one aspect the barrel is rotated at 10 revolutions per minute, however higher and lower speeds are also implemented. The at least one radiating means is activated to emit microwave pulses at a predetermined power-frequency relationship. The pulses are emitted to cause high bacterium, or egg, molecular excitation which weakens their external layer, followed by intensity pulses to make them vibrate more and more in an incremental fashion. This is performed in a constant and monitored manner so as to prevent any wood overheating. Therefore, the pulses may be higher-energy but shorter, or lower-energy but longer, depending on the emission phase in this disinfection process. In this manner, complete disinfection is also accomplished even using only a single radiating means.

In case of a plurality of radiating means, the power of emission is set so that it is lowest at either ends, and highest in the central radiating means. In the case of three radiating means, the power emitted could be, for example, 1000 W/5000 W/1000 W. Also, the frequency of emission is set so that it increases gradually from one end to the other. In the case of three radiating means, the frequency emitted could be, for example, 900 MHz-2450 MHz-5000 MHz.

During the application of the microwave pulses, readings from the sensors are periodically collected by the processing means, uniformity means and by the safety means. The temperature within the chamber is constantly monitored by the processing means and the process is interrupted in case the temperature exceeds a threshold chosen in the range of 65° C. to 70° C. The level of radiation is also constantly monitored by the processing means to ensure it is within normal operating range. The uniformity means uses the radiation level readings to determine whether the radiation is being uniformly applied or not. The safety means also monitors these readings, and interrupts the radiating process in case any of them exceed predetermined thresholds representing a hazard to safety.

After the predefined radiation dosage has been applied, the rotating means stops operating, the doors are unlocked, and the barrel is ready to be removed. In case of dynamic disinfection, the doors open automatically and the loading means transports the barrels out of the chamber.

Figure 4:
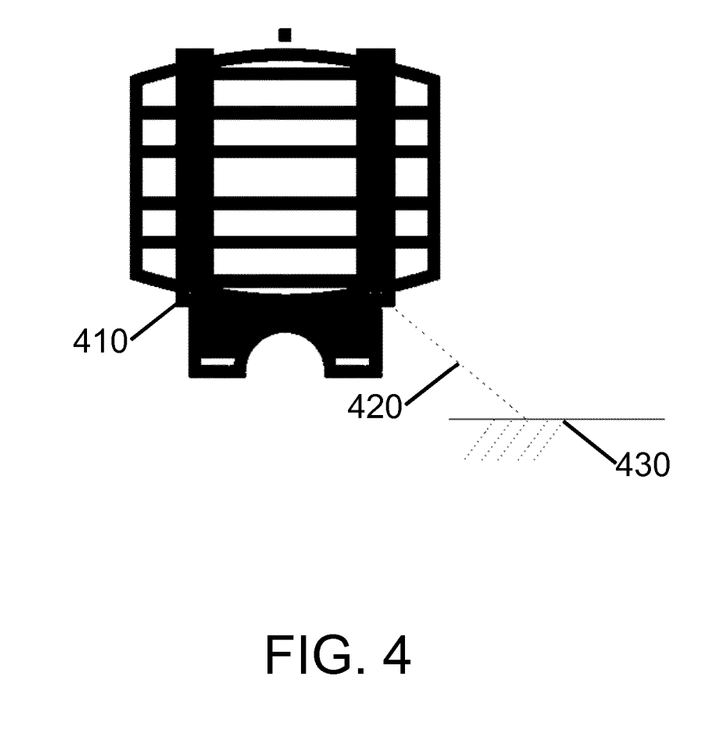
FIG. 4 depicts a grounded disinfection apparatus.

It has been ascertained that the metallic hoops of the barrels heat up by electric current induction and are also statically charged during the radiation. Therefore in one aspect depicted in FIG. 4, any metallic elements 410 of the barrel, such as hoops, are grounded via a direct metallic connection 420 to the ground 430. This prevents dangerous sparks from being generated or the metallic parts from overheating the wood beneath beyond the optimum temperatures.

Figure 5:
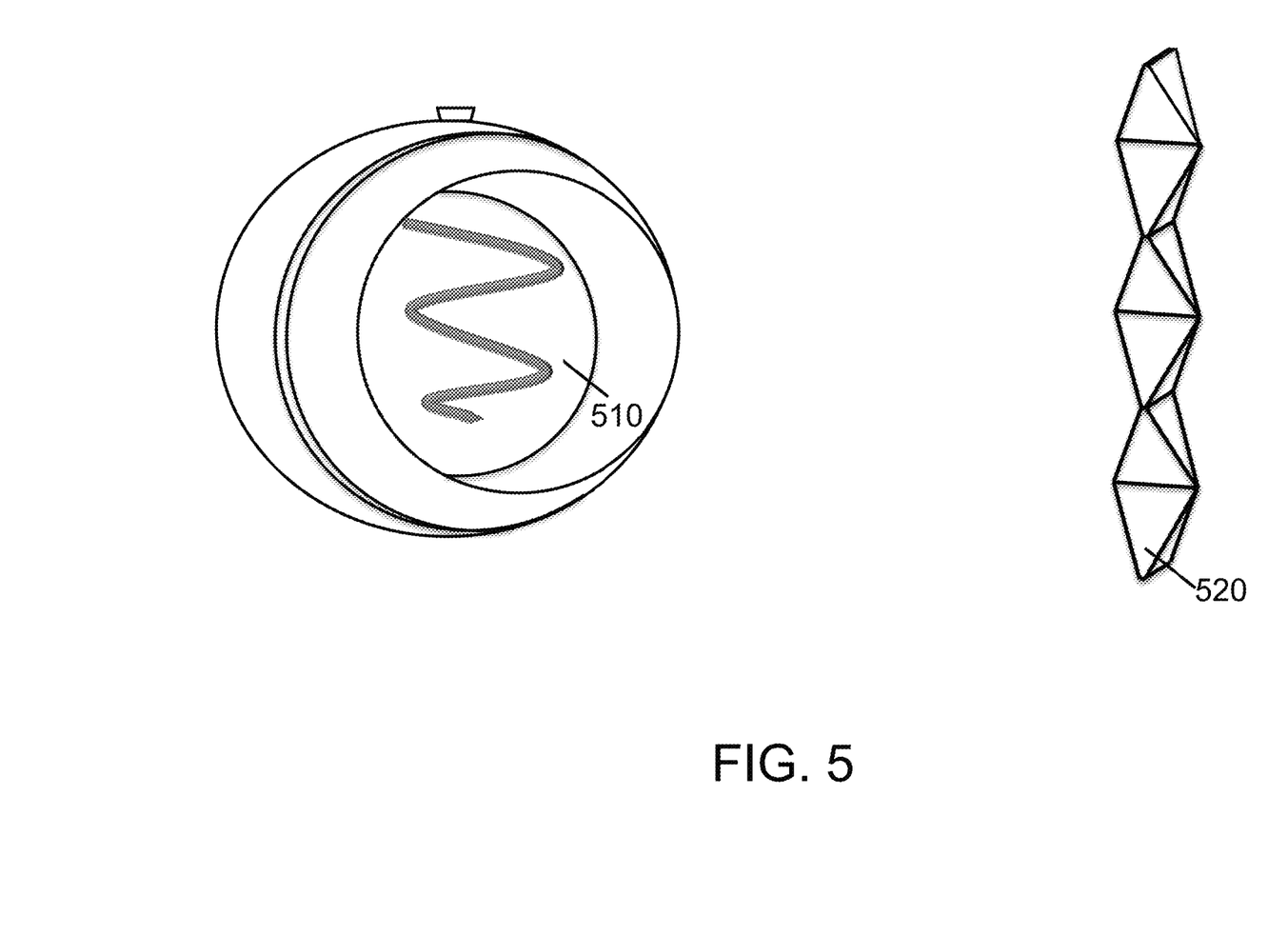
FIG. 5 depicts internal radiating elements of the disinfection apparatus.

Another problem which has been identified is that, due to the conducting properties of the metallic elements of the barrels, they microwave radiation is not applied in full efficiency to the wood below or contiguous to these metallic parts. The disinfection is therefore not complete in these regions. In order to solve this problem, the inventors have developed distribution means which are placed within the barrel or outside the barrel but inside the chamber. FIG. 5 depicts a spiral-shaped distribution means 510 (on the left side of FIG. 5) and a serrated-shaped distribution means 520 (on the right side of FIG. 5). The distribution means reflect the emitted microwave radiation and uniformly distribute it throughout the barrel and chamber. In this manner, all wooden regions, also those normally not fully radiated, receive a complete dosage. Therefore thorough microbial disinfection is thereby guaranteed. The spiral-shaped means reflects the radiation omni-directionally, and therefore ensures all spaces within the barrel are radiated. The serrated-shaped means reflect more linearly, thereby covering precisely those stave regions directly below the metallic elements of the barrels, such as the hoops.

Therefore the different aspects of the invention described provide a novel disinfection apparatus, and corresponding method, for wood barrel disinfection using microwave shock pulse, MwSP, technology for the complete elimination of microbial populations. This is accomplished by a system which ensures deep and complete disinfection, however such that the temperature is maintained below material degradation level. Complete disinfection is achieved due to effectiveness up to the deepest layers. The wooden barrel material is however preserved, due to the non-harmful nature of the dosage regime programmed into the radio frequency emission. It is also a safe procedure, due to the inexistence of contact with operators, as well as inexistence of traces in the food products being carried. Due to its simplicity, on-site treatment is enabled, as the technology permits implementing an easily transportable system for speedy treatment, which is installed on-site at the user's premises, minimising carbon footprint as well as external contamination. This is turn leads to a sustainable system, due to the reduction in resource consumption. It has also been ascertained that this disinfection process crystallizes the topmost humid layer of the internal lining of the barrels, which once removed, a refreshing effect is obtained by opening the pours of the wood, enabling the wooden cask aromas to be made once again available for the next wine maturing process. Hence, the process not only guarantees disinfection but also refreshes the wooden casks, providing once more their aromatic qualities.

What has been described comprises several example embodiments. Since it is not possible or feasible to describe all the variations of combinations and permutations of the inventive concept that would give rise to a large number of embodiments and redundant paragraphs, it is understood that the skilled artisan would derive these different possible permutations and combinations of the different embodiments and aspects described after a direct and objective reading of this disclosure. Therefore, the main aspects and embodiments have been described, understanding that they comprise the remaining combinations, variations and modifications, whilst they are comprised within the scope of protection defined by the claims. The skilled person would understand that the presented description of the embodiments does not limit the invention, nor do the drawings.

In the following, further examples of the invention are provided:
  A disinfecting apparatus for elimination of microbes of a container, the apparatus comprising: a chamber for receiving the container; at least one radiating means for emitting microwave radiation at a predetermined power, at a predetermined frequency, and during a predetermined pulse duration, followed by intensity pulses causing microbe vibration in an incremental fashion; and processing means for controlling the microwave radiation and its parameters.
  The at least one radiating means is activated to emit microwave pulses at a predetermined power-frequency relationship. The pulses are emitted to cause high bacterium, or egg, molecular excitation to make them vibrate more and more in an incremental fashion which weakens their external layer until their destruction. This is performed in a constant and monitored manner so as to prevent any wood overheating. Therefore, the pulses may be higher-energy but shorter, or lower-energy but longer, depending on the emission phase in this disinfection process. In this manner, complete disinfection is also accomplished even using only a single radiating means. This process also ensures no damage to the wood. In one aspect this two-phase emission is implemented by emitting first the low-energy pulses followed by the high-energy intensity pulses. In another aspect the energy is incremented gradually from low-energy to high-energy intensity pulses.
  A disinfecting apparatus for elimination of microbes of a container, the apparatus comprising: a chamber for receiving the container; at least one radiating means for emitting microwave radiation at a predetermined power, at a predetermined frequency, and during a predetermined pulse duration; and processing means for controlling the microwave radiation and its parameters.
  The apparatus, wherein the container has curved sides, or has a cylindrical shape, such as a barrel. The apparatus, further comprising loading means for loading and unloading the container in and out of the chamber, wherein the loading means are vertical means, such as elevators, or horizontal means, such as a running belt or a ramp. The apparatus, further comprising rotating means for rotating the barrel along its longitudinal axis, wherein the rotating means are motor-driven or free-rotating. The apparatus, wherein the chamber is a resonance cavity comprising a microwave antenna configured for constant radiation at a predetermined distance. The apparatus, wherein a plurality of radiating means are configured in linear fashion along the length of the cavity, or wherein a plurality of radiating means are configured in linear fashion along the breadth of the cavity, or wherein a plurality of radiating means are configured in matrix format along the length and breadth of the cavity. The apparatus, wherein at least two of the plurality of radiating means are configured on the sides of the cavity, one on each side, diagonally impinging both flat ends of the barrel. The apparatus, wherein the processing means is configured for setting the frequency of radiation of the plurality of radiating means in increasing frequency along the length of the chamber. The apparatus, wherein the processing means is configured for setting the power of radiation of the plurality of radiating means highest in the central region of the chamber and lowest in the end sections of the chamber. The apparatus, further comprising at least one temperature sensor, or at least one radio frequency sensor or at least one door sensor, or any combination of sensors, and wherein the processing means is configured for controlling the microwave radiation and its parameters as a function of the collected data from at least one sensor. The apparatus, wherein the processing means is configured to interrupt the radiating process once the temperature inside the chamber exceeds 65° C. The apparatus, further comprising uniformity means for detecting zones of non-uniform irradiation, and providing feedback for fine-tuning the emission of microwave pulses ensuring homogenized treatment. The apparatus, further comprising safety means configured for interrupting the radiating process if the readings from any of the sensors exceed a predetermined safety threshold or indicate danger. The apparatus, further comprising at least one distribution means for reflecting microwave radiation uniformly within the container and within the chamber. The apparatus, further comprising a ground connection for earthing at least one metallic element of the container to the ground. The apparatus, further comprising a plurality of coupling components arranged on the lower sides of the cavity and configured to electrically couple the cavity with the chamber's floor.

A method of disinfection for elimination of microbes of a container, the method comprising: receiving the container in a chamber; emitting microwave radiation at a predetermined power, at a predetermined frequency, and during a predetermined pulse duration, followed by intensity pulses causing microbe vibration in an incremental fashion; and controlling the microwave radiation and its parameters.

The microwave pulses are emitted at a predetermined power-frequency relationship. The pulses are emitted to cause high bacterium, or egg, molecular excitation to make them vibrate more and more in an incremental fashion which weakens their external layer until their destruction. This is performed in a constant and monitored manner so as to prevent any wood overheating.

Therefore, the pulses may be higher-energy but shorter, or lower-energy but longer, depending on the emission phase in this disinfection process. In this manner, complete disinfection is also accomplished even using only a single radiating means. This process also ensures no damage to the wood. In one aspect this two-phase emission is implemented by emitting first the low-energy pulses followed by the high-energy intensity pulses. In another aspect the energy is incremented gradually from low-energy to high-energy intensity pulses.

A method of disinfection for elimination of microbes of a container, the method comprising: receiving the container in a chamber; emitting microwave radiation at a predetermined power, at a predetermined frequency, and during a predetermined pulse duration, followed by intensity pulses causing microbe vibration in an incremental fashion; and controlling the microwave radiation and its parameters.

A computer readable medium comprising instructions, once executed on a computer, for performing the steps of receiving the container in a chamber; emitting microwave radiation at a predetermined power, at a predetermined frequency, and during a predetermined pulse duration, followed by intensity pulses causing microbe vibration in an incremental fashion; and controlling the microwave radiation and its parameters.

The invention claimed is:

1. A disinfecting apparatus for elimination of microbes of a container, the apparatus comprising:
    a chamber configured for receiving the container, wherein the chamber is a resonance cavity comprising a microwave antenna configured for constant radiation at a predetermined distance, and wherein the container has curved sides or has a cylindrical shape;
    loading means for loading and unloading the container in and out of the chamber, wherein the loading means are vertical means or horizontal means;
    rotating means for rotating the container along its longitudinal axis, wherein the rotating means are motor-driven or free-rotating;
    at least one radiating means configured for emitting microwave radiation;
    processing means configured for controlling the microwave radiation and its parameters for emitting microwave radiation at a predetermined power, at a predetermined frequency, and during a predetermined pulse duration, followed by intensity pulses causing microbe vibration in an incremental fashion; and
    a ground connection for earthing at least one metallic element of the container to the ground, or a plurality of coupling components arranged on the lower sides of the cavity configured to electrically couple the cavity with the chamber's floor.

2. The apparatus according to claim 1, wherein the at least one radiating means includes a plurality of radiating means, and the plurality of radiating means are configured in linear fashion along the length of the cavity, or wherein the plurality of radiating means are configured in linear fashion along the breadth of the cavity, or wherein the plurality of radiating means are configured in matrix format along the length and breadth of the cavity.

3. The apparatus according to claim 2, wherein at least two of the plurality of radiating means are configured on the sides of the cavity, one on each side, diagonally impinging both flat ends of the container.

4. The apparatus according to claim 1, wherein the at least one radiating means includes a plurality of radiating means, and wherein the processing means is configured for setting the frequency of radiation of the plurality of radiating means in increasing frequency along the length of the chamber.

5. The apparatus according to claim 1, wherein the at least one radiating means includes a plurality of radiating means, and wherein the processing means is configured for setting the power of radiation of the plurality of radiating means highest in the central region of the chamber and lowest in the end sections of the chamber.

6. The apparatus according to claim 1, further comprising a set of one or more sensors including at least one temperature sensor, or at least one radio frequency sensor or at least one door sensor, or any combination of sensors, and wherein the processing means is configured for controlling the microwave radiation and its parameters as a function of the collected data from the set of one or more sensors.

7. The apparatus according to claim 6, wherein the processing means is configured to interrupt the radiating process once the temperature inside the chamber exceeds 65° C.

8. The apparatus according to claim 1, further comprising at least one distribution means for reflecting microwave radiation uniformly within the container and within the chamber.

* * * * *